United States Patent
Graindorge

(10) Patent No.: US 8,874,210 B2
(45) Date of Patent: Oct. 28, 2014

(54) APPARATUS AND METHOD FOR ANALYZING PATIENT TOLERANCE TO A STIMULATION MODE FAVORING A SPONTANEOUS ATRIOVENTRICULAR CONDUCTION

(75) Inventor: Laurence Graindorge, Thouaré-sur-Loire (FR)

(73) Assignee: Sorin CRM SAS, Clamart (FR)

( * ) Notice: Subject to any disclaimer, the term of this patent is extended or adjusted under 35 U.S.C. 154(b) by 759 days.

(21) Appl. No.: 12/813,841

(22) Filed: Jun. 11, 2010

(65) Prior Publication Data

US 2010/0318150 A1 Dec. 16, 2010

(30) Foreign Application Priority Data

Jun. 15, 2009 (FR) ...................... 09 53982

(51) Int. Cl.
*A61N 1/365* (2006.01)
*G06T 15/04* (2011.01)

(52) U.S. Cl.
CPC *G06T 15/04* (2013.01); *A61N 1/365* (2013.01)
USPC ................. 607/17; 600/513; 607/7

(58) Field of Classification Search
USPC ......................................................... 607/18
See application file for complete search history.

(56) References Cited

U.S. PATENT DOCUMENTS

| | | |
|---|---|---|
| 5,304,208 A | 4/1994 | Inguaggiato et al. |
| 5,318,594 A | 6/1994 | Limousin et al. |
| 5,454,838 A | 10/1995 | Vallana et al. |
| 5,496,351 A | 3/1996 | Plicchi et al. |
| 5,549,650 A | 8/1996 | Bornzin et al. |

(Continued)

(56) References Cited

FOREIGN PATENT DOCUMENTS

| | | |
|---|---|---|
| EP | 0488904 | 6/1992 |
| EP | 0515319 | 11/1992 |

(Continued)

OTHER PUBLICATIONS

Foreign Search Report (Annexe Au Rapport De Recherche Preliminaire Relatif A La Demande De Brevet Francais No. FR0953982 FA723276), Apr. 1, 2010.

*Primary Examiner* — Kennedy Schaetzle
*Assistant Examiner* — Erica Lee
(74) *Attorney, Agent, or Firm* — Foley & Lardner LLP

(57) ABSTRACT

An implantable cardiac prosthesis device conducting an analysis of a patient tolerance to a pacing mode favoring the spontaneous atrioventricular conduction is disclosed. The device operates in a dual chamber (DDD or biventricular) mode and in a pacing mode favoring the spontaneous atrioventricular conduction such as an AAI mode (10) with a ventricular sensing or a mode with hysteresis of the atrioventricular delay. The device controls (10-18) the conditional switching from one mode to the other. The device comprises a hemodynamic sensor, including an endocardial acceleration sensor, derives a hemodynamic index representative of the hemodynamic tolerance of the patient to the spontaneous atrioventricular conduction. The device controls inhibiting or (20) forcing the conditional switching of the device to the DDD (or biventricular) mode according to the evolution of the hemodynamic index.

22 Claims, 3 Drawing Sheets

(56) References Cited

U.S. PATENT DOCUMENTS

| | | |
|---|---|---|
| 5,693,075 A | 12/1997 | Plicchi et al. |
| 6,604,002 B2 | 8/2003 | Molin |
| 6,622,039 B1 | 9/2003 | Ripart et al. |
| 6,725,091 B2 | 4/2004 | Dal Molin |
| 7,076,297 B2 | 7/2006 | Limousin et al. |
| 7,164,946 B2 | 1/2007 | Amblard et al. |
| 7,366,566 B2 | 4/2008 | Henry et al. |
| 2005/0240235 A1 | 10/2005 | Limousin |
| 2006/0079940 A1* | 4/2006 | Ripart ............... 607/9 |
| 2007/0005113 A1* | 1/2007 | Casavant et al. ............ 607/9 |
| 2007/0135849 A1 | 6/2007 | Hallier et al. |
| 2007/0135850 A1 | 6/2007 | Amblard |
| 2009/0209875 A1* | 8/2009 | Giorgis et al. ............ 600/512 |
| 2009/0276001 A1* | 11/2009 | Busacker et al. ............ 607/28 |

FOREIGN PATENT DOCUMENTS

| | | |
|---|---|---|
| EP | 0582162 | 2/1994 |
| EP | 0655260 | 5/1995 |
| EP | 1059099 | 12/2000 |
| EP | 1116497 | 7/2001 |
| EP | 1138346 | 10/2001 |
| EP | 1346750 | 9/2003 |
| EP | 1470836 | 10/2004 |
| EP | 1550480 | 7/2005 |
| EP | 1731194 | 12/2006 |
| EP | 1731195 | 12/2006 |

* cited by examiner

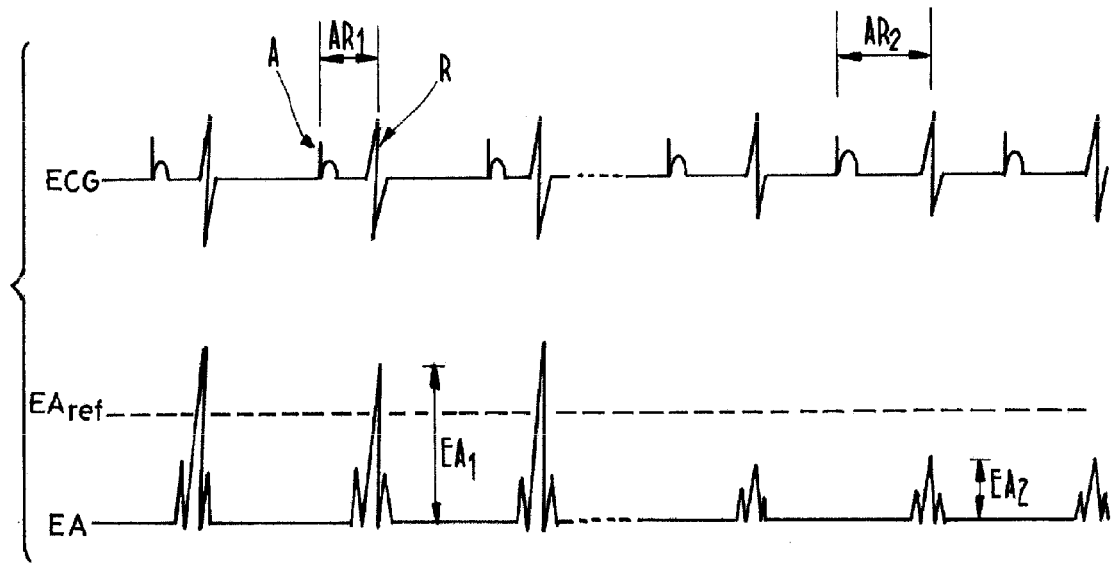
FIG_1
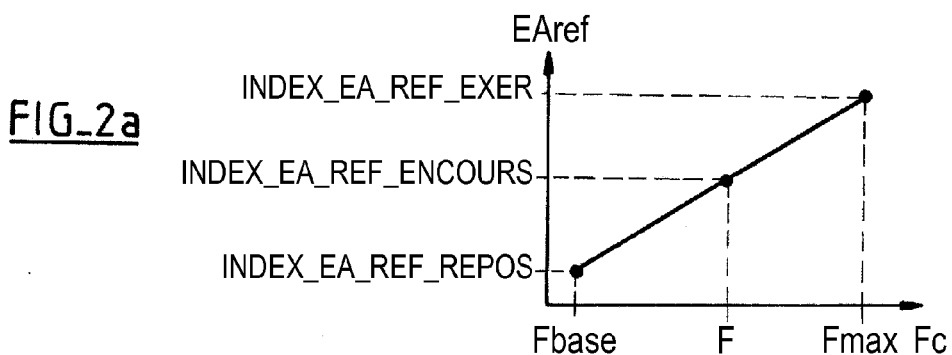
FIG_2a
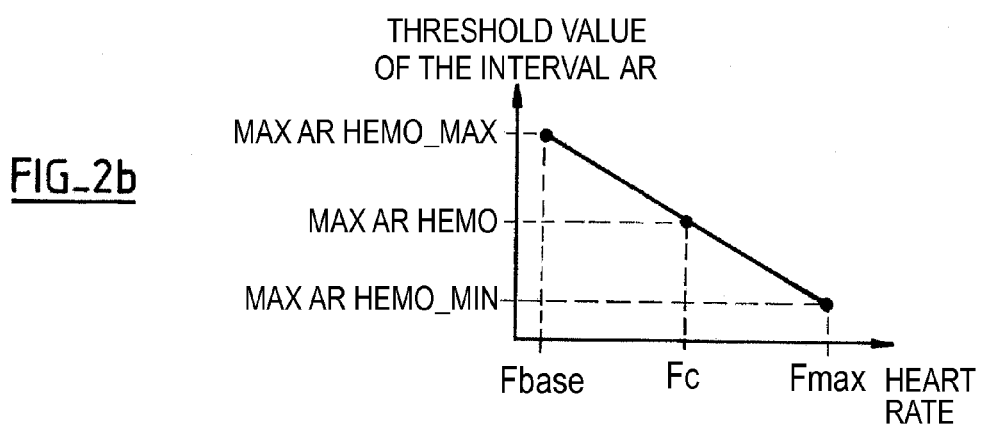
FIG_2b

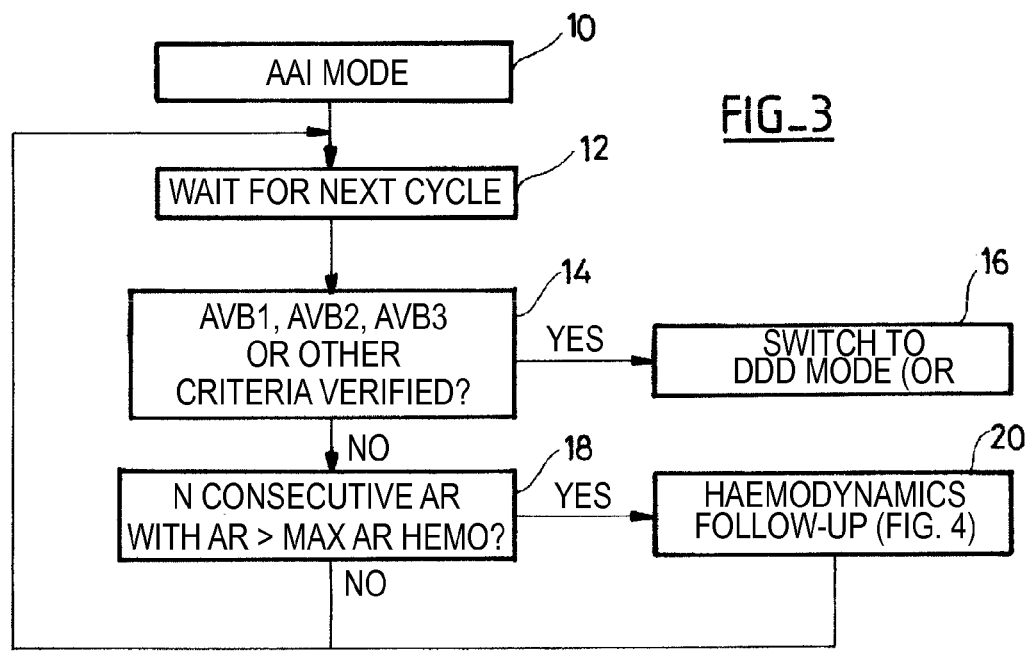
FIG_3
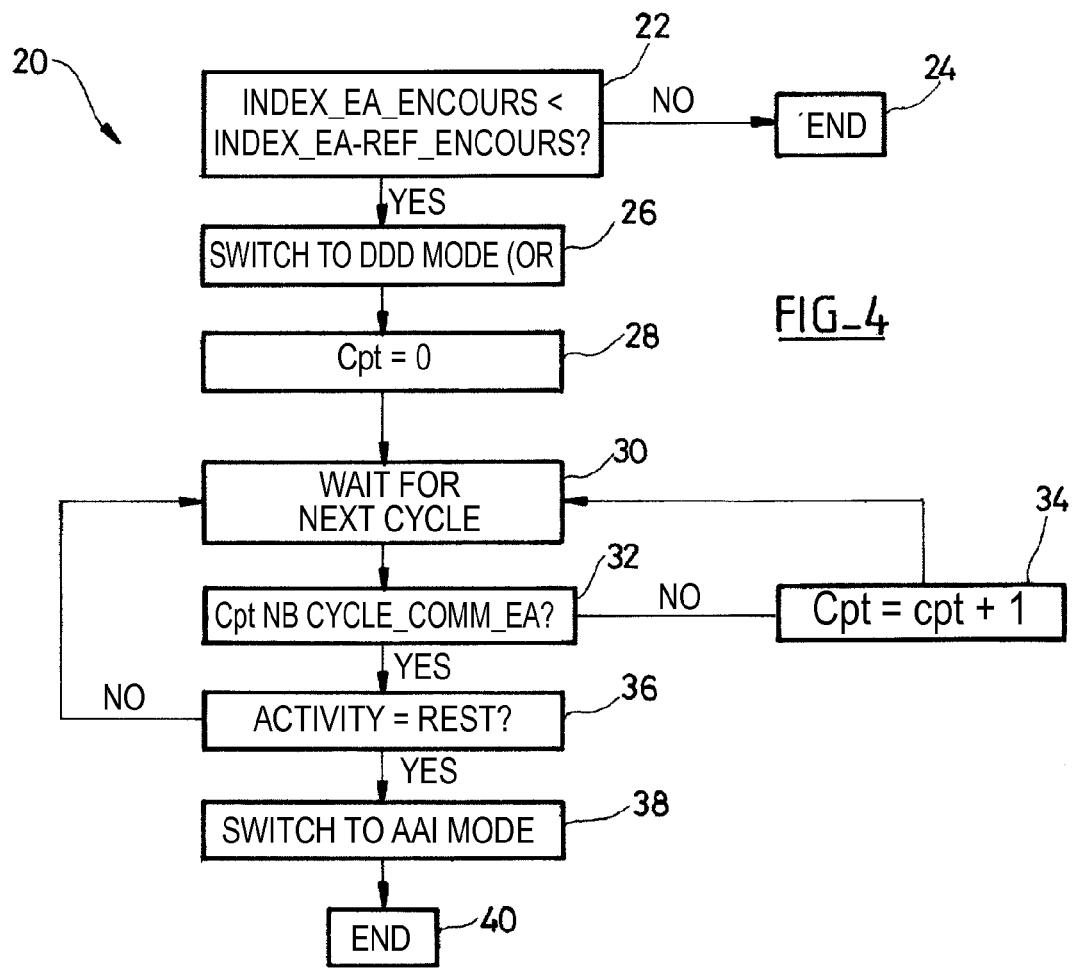
FIG_4

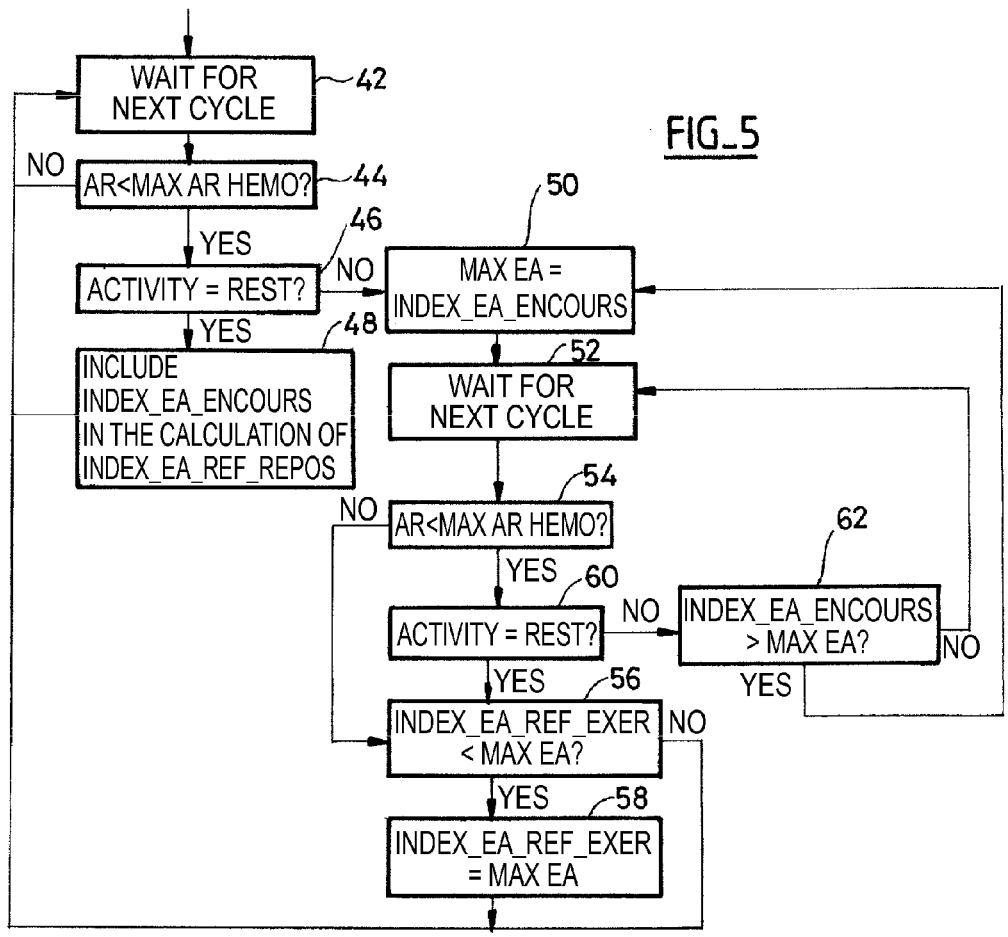
FIG_5
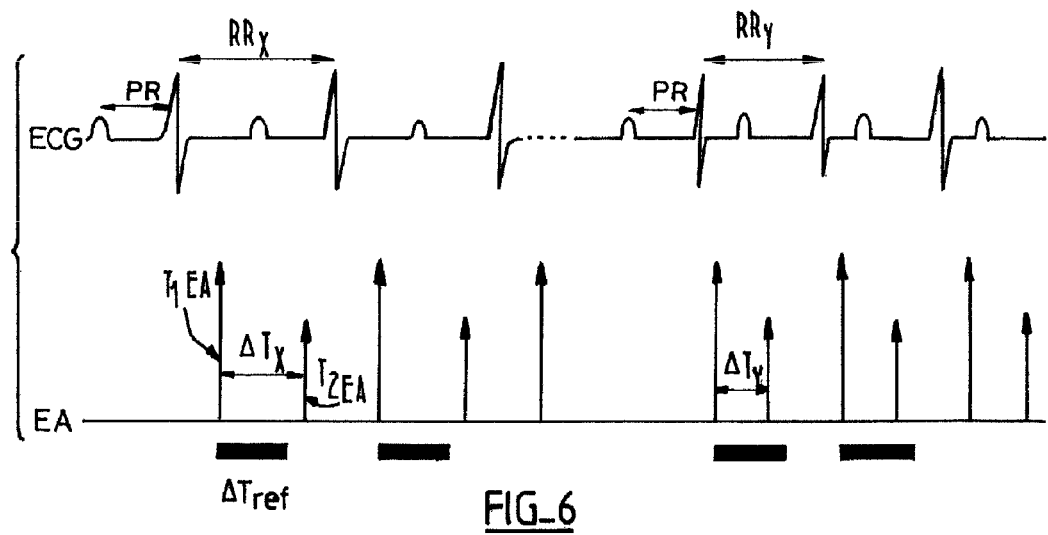
FIG_6

APPARATUS AND METHOD FOR ANALYZING PATIENT TOLERANCE TO A STIMULATION MODE FAVORING A SPONTANEOUS ATRIOVENTRICULAR CONDUCTION

CROSS-REFERENCE TO RELATED APPLICATIONS

The present application claims the benefit of and priority to French Patent Application No. 0953982, filed Jun. 15, 2009.

FIELD OF INVENTION

The present invention is directed to an "active implantable medical device" as defined by the 20 Jun. 1990 Directive 90/385/EEC of the Council of the European Communities, including implantable cardiac prosthesis devices such as cardiac pacemakers, defibrillators and/or cardioverters that continuously monitor a patient's heart rhythm and deliver, if necessary, at the patient's heart electrical stimulation, resynchronization, cardioversion and/or defibrillation pulses in case of a rhythm disorder detected by the device, and more particularly those devices that include circuitry for stimulation and detection in both the atrium and ventricle.

BACKGROUND

The basic mode of operation of an active implantable medical device known as a cardiac prosthesis device is an AAI mode—or more precisely 'pseudo-AAI mode'—with single chamber atrial pacing (AAI mode in the strict sense) and monitoring of ventricular activity. This mode is normally maintained as long as an atrioventricular conduction is normal, i.e., as long as each atrial event (e.g., atrial detection corresponding to spontaneous activity, atrial pacing corresponding to a stimulation) is followed by an associated ventricular detection.

However, when the device operates in a "dual chamber" mode, after an atrial event—whether it is a spontaneous atrial depolarization (detection of a P wave) or stimulated atrial depolarization (delivery of an A pulse)—the device simultaneously monitors ventricular activity and starts measuring a delay called "atrioventricular delay", commonly referred to as AVD. If at the end of the AVD, no spontaneous ventricular activity (R wave) is detected, then the device triggers a stimulation of the ventricle (application of a V pulse).

Recent clinical studies have demonstrated that for preventing an occurrence of heart failure or atrial fibrillation among patients with dual chamber pacemakers, it is recommended to avoid as much as possible right ventricular pacing. This is done to preserve an intrinsic AV conduction in patients who have otherwise no permanent conduction disorder requiring the use of a permanent ventricular pacing.

In this respect, recent cardiac prosthesis devices implemented a new stimulation mode that emphasizes a spontaneous ventricular conduction, and permits an operation with a long AVD that increases the time in which a potential spontaneous ventricular conduction may occur—but in return accepts the risk of maintaining the symptomatically long AVD.

Some pacemakers, for example, of the type described in EP 0 488 904 and its US counterpart U.S. Pat. No. 5,318,594 (ELA Medical, now known as Sorin CRM) are equipped with AVD hysteresis algorithms that are used in a DDD mode to stimulate patients not having conduction disorders. These devices can operate in two modes, DDD or AAI (the AAI mode being a DDD mode modified by lengthening the AV delay), and are provided with a mode called "DDD-CAM" providing automatic mode switching (CAM) of DDD to AAI and vice versa. The value of the AVD is not fixed but varies linearly between a maximum value, used when the heart rate is near the rest frequency, and a minimum value, used when the heart rate is near its maximum value. The details of this adaptation of AVD is described for example in EP 1 059 099 A and its US counterpart U.S. Pat. No. 6,622,039 (ELA Medical, now known as Sorin CRM). The basic idea of the AVD hysteresis algorithm is to extend the value of AVD under certain criteria, to which favors the occurrence of a potential spontaneous rhythm: the AVD can thus be lengthened to avoid unnecessary ventricular pacing or gradually reduced if no spontaneous rhythm is found, to return to a normal value of conventional DDD stimulation.

This technique preserves the natural conduction in some patients, but has been found to be of a limited use in other patients especially those with sinus dysfunction because the limits of the hysteresis make it difficult to discover the spontaneous rhythm.

To overcome this limitation, a new pacing mode called "AAIsafeR" has been developed in more recent devices, whose basic principle is explained in EP 1 346 750 and its US counterpart U.S. Pat. No. 7,164,946 (ELA Medical, now known as Sorin CRM). In an AAIsafeR mode, the device operates in an AAI mode and the ventricular activity is constantly monitored to detect an occurrence of atrioventricular blocks (AVB) that cause a temporary disorder of depolarization of the ventricle. In this case, because a number of conditions are met, the device automatically switches to a DDD mode, with operating parameters optimized for this temporary AVB condition. In a multisite device, the switching is instead made to a biventricular stimulation mode (also referred to as a "BiV" mode), named "AAISafeRR". After the AVB condition disappeared, and thus the atrioventricular conduction was restored, the device automatically returns to the AAI mode when a number of other conditions are met. The AAIsafeR (or AAISafeRR) mode also includes a switching criterion linked to the detection of an AV block of the first type or AVB1, that is to say, the presence of a too long AVD: when the device detects, for example, more than six consecutive cycles of a too long AVD (typically longer than 350-450 ms), then the device switches to a DDD mode, or in a similar way, to a biventricular mode on a multisite device.

The AAIsafeR (or AAISafeRR) mode preserves the natural conduction very efficiently, and the clinical results show a percentage of residual ventricular pacing close to zero. Various improvements have been made, for example, to eliminate an incidence of premature ventricular contractions (See EP 1 470 836 and its US counterpart U.S. Pat. No. 7,076,297 (ELA Medical, now known as Sorin CRM)) and/or paroxysmal AV block (See EP 1 550 480 A and its US counterpart U.S. Pat. No. 7,366,566 (ELA Medical, now known as Sorin CRM), or in the presence of ventricular events of uncertain nature occurring during the safety window (See EP 1 731 195 A and its US counterpart U.S. Published Application No. 2007/0135849. ELA Medical, now known as Sorin CRM), or in the presence of ventricular tachycardias (See EP 1 731 194 A and its US counterpart U.S. Publication No. 2007/0135850, ELA Medical, now known as Sorin CRM).

One of the peculiarities of the AAIsafeR (or AAISafeRR) pacing mode is to allow a very long AVD, which is programmable. But such delays can be more or less well tolerated by the patient, or can be tolerated under certain conditions (e.g., at rest) and less tolerated in others (e.g., during exercise). In patients suffering from brady-tachycardia and taking antiarrhythmic drugs, an appearance of symptoms related to a too long AVD in AAI mode were notably reported.

In some patients, the risk of stimulating the right ventricle too often must be balanced with the risk of developing symptoms by the use of a too long AVD. In the absence of specific criteria, this risk is assessed as a function, for example, of the patient's ejection fraction, and possibly based on symptoms reported at follow-up visits, but, in any event, is never based on the instantaneous situation of the patient.

Moreover, these difficulties linked to a too long AVD time may be only transient and only occur, for example, during certain patient activity, or only for some patients during atrial pacing and not after a spontaneous P wave. In such cases, it would be detrimental to permanently program a short AVD to overcome these transients.

It is therefore, an object of the present invention to provide a cardiac prosthesis device equipped with a pacing mode favoring a spontaneous conduction of a patient (including a device of the AVD hysteresis type or a device of the AAIsafeR (or AAISafeRR type), which overcomes the difficulties and limitations outlined above, related to considered a long AVD in case of AVB1.

SUMMARY

Broadly, the present invention is directed to the use of an hemodynamic sensor, typically (but not limited to) an endocardial acceleration (EA) sensor to monitor and assess the patient's tolerance to a long AVD, so as to determine if the intrinsic conduction is tolerated or not, and depending on the result of this assessment change the criteria to switch to a DDD mode (or to a BiV mode in multisite devices). This is done to maximize the chances of maintaining a spontaneous ventricular conduction as long as it is tolerated by the patient, while minimizing the risk of allowing a symptomatically long AVD.

More specifically, in terms of cardiac mechanics, the AVD must be long enough to allow a complete contraction of an atrium and thereby empty the blood contained by the atrium into a ventricle, and a ventricular contraction once the atrial contraction is fully completed. But the ventricular contraction should not occur too long after, as a too long AVD could dissociate the atrium/ventricle system, with the risk of triggering arrhythmias by a retrograde conduction, or reducing the hemodynamic effectiveness of the cardiac cycle. Indeed, as the atrial contraction completes the ventricular filling, the delay between the end of the filling and the onset of the ventricular emptying is "lost" time, from a hemodynamic point of view. In addition, any extended period of AVD impacts the ventricular diastole (ventricular filling post-emptying) and delays the end of this ventricular filling, which then overlaps the next atrial contraction. It is therefore important to better adapt the AVD for each patient, so that the onset of ventricular emptying (caused by the stimulation of the ventricle) occurs immediately after the filling of the ventricle by the atrium.

Hemodynamic sensors are distinguished from activity sensors (e.g., accelerometers) and metabolic sensors (e.g., minute ventilation sensors) that are used for diagnosing the presence or absence of an exercise by the patient and for quantifying its metabolic needs, for example, to adapt the heart rate of stimulation according to the detected level of effort or activity.

Hemodynamic sensors such as endocardial acceleration sensor or bioimpedance sensor, may not only monitor the patient effort as the activity and/or metabolic sensors described above, but also give an indication of the patient's hemodynamic tolerance in relation with a certain event (e.g., ventricular arrhythmia), with drugs, or possibly with a modification of the AVD.

U.S. Pat. No. 5,549,650 (Bornzin, et al./Pacesetter, Inc.) describes a pacemaker comprising a hemodynamic sensor, designed to adapt a value of AVD. The technique described therein is only intended to modify so as to optimize the value of AVD according to the patient response. The object of the present invention is instead to use the hemodynamic sensor not (or not only) for controlling the value of a long AVD, but also to control the switching to a DDD (or BiV) mode: either by faster switching to the DDD (or BiV) mode if the value of the long AVD is—from an hemodynamic point of view—not well tolerated by the patient or, conversely, to inhibit the switching to the DDD (or BiV) mode to maintain the conduction if the long AVD is well tolerated. In a similar way, for a multisite device, the present invention regulates the switching to a biventricular mode.

One aspect of the present invention is directed to an active implantable medical device for cardiac stimulation, resynchronization and/or defibrillation, comprising: means for detecting spontaneous atrial and ventricular events; means for delivering ventricular and atrial pacing stimulation pulses; means for operating the device in a DDD and/or a biventricular mode with ventricular sensing and ventricular pacing in the absence of spontaneous ventricular depolarization detected after an atrioventricular delay, and means for mode switching, to conditionally control, according to predetermined criteria, the switching of the device between the DDD (or BiV) mode and a pacing mode emphasizing the spontaneous atrioventricular conduction and inversely back to the pacing mode from the DDD (or BiV) mode.

Preferably, the device of the invention includes a hemodynamic sensor having an output signal, means for deriving from the output signal a hemodynamic index representative of the patient's tolerance to a spontaneous atrioventricular conduction, and means for inhibiting, or for forcing, said switching of the device to the DDD (or BiV) mode based on said hemodynamic index.

The pacing mode favoring the spontaneous atrioventricular conduction to the DDD (or BiV) mode preferably is either an AAI mode with ventricular sensing, or a DDD (or BiV) mode with hysteresis of the AVD.

According to an advantageous embodiment of the present invention, the device optionally comprises diagnostic means for determining an occurrence of an atrioventricular block, and means for inhibiting, or for forcing the switching of the device to the DDD (or BiV) mode, the diagnostic and inhibiting means being selectively activated only in the absence of an atrioventricular block detected by the diagnostic means.

In another embodiment, the device comprises means for evaluating a current value of the AR interval separating an atrial pacing from the consecutive spontaneous ventricular depolarization, means for comparing the current value of the AR interval to a first threshold, means for inhibiting or forcing the conditional switching of the device to the DDD (or BiV) mode, said evaluating, comparing, and inhibiting means being selectively activated only if the current value of the AR interval is greater than the first threshold. In this case, the first threshold is a variable threshold, for example, depending on the heart rate, and the device further comprises means for dynamically reducing the value of the first threshold when the current heart rate is increased.

Yet another embodiment of the present invention provides that the device further comprises means for detecting a state of patient effort; wherein the means for inhibiting or forcing the switching of the device to DDD (or BiV) mode, in response to having forced a switch to DDD (or BiV) mode, inhibits the return to the pacing mode favoring the spontaneous atrioventricular conduction as long as the device detects a state of patient effort.

In a preferred embodiment, the means for inhibiting or forcing, the switching of the device to the DDD (or BiV) mode operates to compare the current value of the hemodynamic index to a reference hemodynamic index, and to force the device to switch to the DDD (or BiV) mode when the current value of the index is less than the reference hemodynamic index. In this case, the value of the reference hemodynamic index is a variable value depending on the heart rate. The device further comprises means for dynamically increasing the value of the reference hemodynamic index when the current heart rate is increased. More preferably this particular value controllably varies between a minimum and a maximum limit. The device further comprises means for dynamically updating said minimum and maximum limits.

In another embodiment of the present invention, the device comprises diagnostic means for determining an appearance of a permanent atrioventricular block, such that the value of the reference hemodynamic index is forced to a value independent of the heart rate in the presence of an atrioventricular block detected by the diagnostic means. Preferably, the hemodynamic sensor is one of an endocardial acceleration sensor or an epicardial acceleration sensor, a myocardium wall motion sensor, an intracardiac pressure sensor, an intracardiac bio-impedance sensor, an optical sensor for measuring oxygen saturation, or a sensor for measuring volume change by ultrasound. In the case of an endocardial accelerometer delivering a signal representative of the movements produced by cyclical contractions of the myocardium, the device includes means for recognizing and isolating in the signal emitted by the sensor a component corresponding to a peak of endocardial acceleration associated with the ventricular contraction, and for deriving said hemodynamic index based on the amplitude of said component. In an alternative implementation, the device includes means for recognizing and isolating in the signal delivered by the sensor at least two components corresponding to two respective peaks of endocardial acceleration associated to the ventricular contraction, and for deriving said hemodynamic index from a time interval separating these two components.

In the context of the present invention, it should be understood that the term "dual chamber" mode is intended to mean a pacing mode that provides atrial sensing and atrial stimulation, and ventricular sensing and ventricular stimulation, and thus broadly includes both an operation in a DDD mode for a conventional dual chamber cardiac prosthesis, and a BiV mode for a multisite cardiac prosthesis device.

BRIEF DESCRIPTION OF THE DRAWINGS

Further features, advantages and characteristics of the present invention will become apparent to a person of ordinary skill in the art in view of the following detailed description of preferred embodiments of the invention, made with reference to the drawings annexed, in which like reference characters refer to like elements.

FIG. 1 is a series of two timing diagrams illustrating an exemplary electrocardiogram (ECG) of a patient and the corresponding endocardial acceleration (EA) signal, collected during a series of successive heart cycles, for a patient with paroxysmal AVB1;

FIG. 2a shows the linear relationship linking the reference value of the index EA to the heart rate;

FIG. 2b shows the linear relationship linking the threshold of the AR interval beyond which the device evaluates the hemodynamic tolerance, to the heart rate.

FIG. 3 is a flowchart of the operation of a pacemaker of the AAIsafeR type in accordance with the present invention;

FIG. 4 is a flowchart of an algorithm for monitoring the hemodynamic tolerance according to the present invention;

FIG. 5 is a flowchart of the reference values learning algorithm used for hemodynamic monitoring in accordance with the present invention; and FIG. 6 is a series of two timing diagrams illustrating an exemplary ECG of a patient and the corresponding EA signal, collected during a series of successive cardiac cycles, in the case of a patient with a permanent AVB1.

DETAILED DESCRIPTION OF THE INVENTION

Examples of implementation of the present invention will now be described with reference to the drawings FIGS. 1-6.

Regarding the software-related aspects of the present invention, the functionality and processes of the present invention may be implemented by an appropriate programming of the software of a known implantable pulse generator, for example, a pacemaker or defibrillator/cardioverter, comprising means for acquiring a signal provided through endocardial leads and/or various sensors monitoring the status of the patient.

In one embodiment, the present invention is applied to the commercial implantable devices marketed by Sorin CRM, Clamart France, such as Reply and Paradym brand devices and comparable commercial and/or proprietary devices of other manufacturers. These devices are equipped with programmable microprocessors, including circuits intended to acquire, format and process electrical signals collected by implanted electrodes and various sensors, and deliver pacing (stimulation) pulses to implanted electrodes. It is also possible to upload towards these devices, by telemetry, pieces of software (i.e., a software control module) that are stored in internal memory and run so as to implement the intended features and functionality of the present invention, as described herein. Implementing the features of the present invention into these devices is believed to be easily feasible by a person of ordinary skill in the art, and will therefore not be described in detail in this document.

The present invention is particularly applicable to a device such as a pacemaker or defibrillator equipped with an algorithm to preserve a spontaneous conduction (e.g., an algorithm of the AAIsafeR type or an algorithm with hysteresis of the DDD-CAM type) and one or more physical (e.g., accelerometer G) and/or physiological (e.g., minute ventilation MV) sensors to distinguish periods of patient activity (e.g., exercise or effort) from periods of patient rest.

In one embodiment, the device of the present invention further includes a hemodynamic sensor for estimating changes in contractility, correlated with increases in blood pressure. The hemodynamic sensor may be an endocardial acceleration sensor of a Peak Endocardial Acceleration (PEA) type as described, for example, in EP0515 319 (US counterpart, U.S. Pat. No. 5,304,208), EP0582162 (U.S. counterpart U.S. Pat. No. 5,454,838) or EP0655260 (US counterpart U.S. Pat. No. 5,496,351) (all three assigned to Sorin Biomedical Cardio SpA. EP0515 319 (US counterpart U.S. Pat. No. 5,304,208) describes how to collect an endocardial acceleration (EA) signal using an endocardial lead equipped with a distal electrode of stimulation implanted to the apex of the ventricle, also incorporating a micro-accelerometer to measure the endocardial acceleration. EP0655260

(US counterpart U.S. Pat. No. 5,693,075) describes a method to process the measured EA signal to derive two values of peak endocardial acceleration corresponding to the two major noises recognizable in each cycle of a healthy heart.

More specifically, the first peak endocardial acceleration ("PEA1") corresponds to the closure of the mitral and tricuspid valves, at the beginning of an isovolumetric ventricular contraction (systole). The variations of this first peak PEA1 are closely related to the pressure changes in the ventricle, therefore is a parameter representative of the myocardial contractility. The amplitude of the first peak PEA1 is, more precisely, correlated with the positive maximum pressure change dP/dt in the left ventricle.

The second peak of endocardial acceleration ("PEA2") corresponds to the closure of the aortic and pulmonary valves at the phase of an isovolumetric ventricular relaxation. This second peak PEA2 is produced by the sudden deceleration of the blood mass in motion in the aorta, and therefore is a parameter representative of the peripheral blood pressure at the beginning of the diastole.

Alternatively, the hemodynamic sensor may be a sensor of intracardiac impedance, such as a sensor for measuring bioimpedance (BioZ), for example, the one disclosed in EP1 116 497 (US counterpart U.S. Pat. No. 6,604,002) or EP1 138 346 (US counterpart U.S. Pat. No. 6,725,091) (both in the name ELA Medical, now known as Sorin CRM). Specifically, EP1116497 (US counterpart U.S. Pat. No. 6,604,002) describes a method to perform a dynamic measurement of a bioimpedance signal to assess the diastolic and systolic volumes, and thus obtain an indication of the cardiac output and thus of the ejection fraction. This document describes in particular a technique for measuring a transvalvular bioimpedance (an impedance between the atrium and the ventricle located on the same side of the heart) by a tripolar configuration, with injection of a current pulse between an atrial site and a ventricular site, and collection of a differential potential between the atrial site and the ventricular site, with one of these sites common to the injection and the collection, a dedicated site of injection and a dedicated site of collection. The injected current is of a low magnitude, insufficient to excite the heart cells.

EP1138346 (US counterpart U.S. Pat. No. 6,725,091) describes another type of bio-impedance measurement, namely a transeptal bioimpedance, an impedance between a site located on one side of the heart and a site on the other side of the heart. This technique also helps deliver a signal representative of the ejection fraction, although the signal is weaker than a transvalvular bioimpedance signal, and it is also influenced by the impedance of the septum tissues.

In the following description of the examples describing an endocardial acceleration sensor, it should be understood that these teachings are transferable to other types of acceleration sensors, e.g., an epicardial sensor or a sensor of wall motion of the myocardium, or generally any other type of sensor delivering a signal representative of the hemodynamic behavior of the myocardium, such as an intracardiac bioimpedance sensor or a pressure sensor. These sensors are designed to assess the hemodynamic tolerance of the patient to a long AVD not only to adjust the value of the AVD, but also to switch more quickly to a DDD mode if the value is not well tolerated, or, conversely, to preserve the intrinsic conduction and prevent or delay the switching to the DDD mode if the AVD is hemodynamically tolerated.

A long AVD is a situation characteristic of a potential AVB1. Specifically, a first-degree AV block or AVB1 corresponds to a present, but delayed conduction. It is distinguished from: (i) the second degree AVB (AVB2), which is characterized by an incomplete conduction with a gradual lengthening of the PR (or AR) interval so that a part of the P waves is no longer conducted; (ii) the complete AV block or third degree AVB (AVB3) which is manifested by completely blocked atrial waves (stimulated or spontaneous), in other words atrial events that are not followed by a ventricular depolarization, and (iii) the ventricular pause, when the interval separating two ventricular events exceeds a specified period, e.g., more than three seconds, or when the ventricular pause is not originated from a disorder of the atrioventricular conduction.

An AVB1 may be paroxysmal or permanent. A paroxysmal AVB1 is intermittent, and typically occurs during phases of sleep or stress, and spontaneously disappears at the end of effort or during wake-up. In contrast, a permanent or quasi-AVB reveals a chronic disorder that must be adequately taken into account.

Implementation of the Invention in Case of a Paroxysmal AVB1

With reference to FIG. 1, the upper timing diagram illustrates an endocardial electrocardiogram (ECG) with, for each cardiac cycle, a stimulated atrial wave A, followed by a spontaneous ventricular depolarization wave R. In the first cycles, the delay AR1 between stimulation A and detection R is shorter than the delay AR2 in a later cycle, indicating an increased intrinsic conduction AV delay. The lower timing diagram provides a hemodynamic signal, typically the endocardial acceleration (EA) signal corresponding to the ECG signal in the upper diagram. In the example shown, the chosen representative parameter is the amplitude EA1, EA2 . . . of the EA signal at the instant of the QRS complex, that is to say, the first peak of endocardial acceleration PEA1 corresponding to the first major noise at the beginning of the phase of an isovolumetric ventricular contraction. It is known that the amplitude variations of the first peak PEA1 are closely related to changes in pressure in the ventricle and therefore is a parameter representative of the myocardium contractility. The dashed line indicates a reference amplitude $EA_{ref}$ to differentiate a good hemodynamic tolerance (e.g., $EA1 > EA_{ref}$) and a poor hemodynamic tolerance (e.g., $EA2 < EA_{ref}$).

Thus it can be seen that for the delay AR1 the amplitude EA1 being greater than the reference value indicates that the delay AR1 is tolerated, thus does not require any special action of the device or change in mode. In contrast, for the AR2 which is a longer delay than the AR1, the corresponding amplitude EA2 is less than the reference value $EA_{ref}$. This indicates that the delay AR2 is not tolerated, thus requires ventricular pacing to prevent symptoms related to AVB1.

The principle of the present invention is to use the correlation between AVD and the peak amplitude of the signal (e.g., EA and/or of other relevant parameters such as the amplitude of the second peak, the interval between the first and second peak) as an index or marker of hemodynamic tolerance of the patient to a long AVD.

This index or marker is designated Indice_EA. A reference hemodynamic index value is defined by averaging the hemodynamic index at rest and during exercise, for normal values of AVD, that is to say in the absence of an AVB1 (i.e., for values of AVD below a threshold value, hereinafter referred to as MaxARhemo beyond which the hemodynamic tolerance is assessed). The reference hemodynamic index value thus determined is a variable depending on the patient's activity, for example, a linear variation between a value at rest and a value during effort. Once this reference value is set, and when a long AVD is experienced (the delay AR is above the threshold MaxARhemo), the device compares the current index to the reference index. For convenience, the term "index" is exchangeably used to refer to the "hemodynamic index".

If the current index is less than the reference index, the device considers that there is no hemodynamic tolerance and that the patient is considered to experience or is at the risk of having a symptomatic AVB1. In this case, it is necessary to stimulate the ventricle to recover a satisfactory hemodynamic situation. The device then switches to a DDD mode (in the case of an AAIsafeR or equivalent device) or shortens the AVD (in the case of a device with hysteresis of the AVD). In the following description of the present invention, it should be understood that by switching to a DDD mode also represents switching to a BiV mode in the case of a multisite device. The device remains in the DDD mode for a predetermined period and/or until the end of the situation of effort, then switches back to the AAI mode (or extends again the AVD in the case of a device with hysteresis). Otherwise, the device considers that the intrinsic conduction is tolerated by the patient, and forces the device to remain in the AAI mode (or inhibits the shortening of the AVD in the case of a device with hysteresis).

The procedure for operating the device depending on the hemodynamic index is now described in more detail, with reference to FIGS. 2 to 5.

FIG. 2a illustrates the relationship between the reference value of $EA_{ref}$, the Indice_EA_ref_encours, and the heart rate Fc. For some choice of the hemodynamic index, the reference value is fixed and the amplitude of the first peak of the signal EA (PEA1) is chosen, thus it is desirable to modify the threshold value $EA_{ref}$ depending on the level of effort. As the amplitude of the first peak of the EA signal increases when the heart rate increases, it is logical to adapt the threshold value $EA_{ref}$.

As shown in FIG. 2a, this index $EA_{ref}$ varies linearly between a minimum value (designated Indice_EA_ref_repos), corresponding to a heart rate near the base rate $F_{base}$, and a maximum value (designated Indice_EA_ref_exer) used when the heart rate is close to the maximum heart rate $F_{max}$. Between these two extremes, each instantaneous heart rate value F of the heart rate $F_c$ corresponds to an instantaneous value of the reference index $EA_{ref}$ designated Indice_EA_ref_encours. It is noted that the linear relationship is chosen for its simplicity, but this relationship is not limited to a linear relationship and other indexes or other types of hemodynamic sensors may correspond to other functional and non-linear relationships.

FIG. 2b illustrates the relationship linking the threshold of the AR interval beyond which the hemodynamic tolerance is analyzed, to the instant heart rate $F_c$. This threshold value, designated MaxARhemo, is the limit delay AR beyond which the device considers that the patient exhibits or is at risk of AVB1. Therefore, beyond the limit delay AR it is necessary to analyze the hemodynamic tolerance to the long AR delay. In a simplified implementation, this value may be fixed, for example, at a value in the range between about 400 or 450 ms. However, even if the fixed value is well adapted to a condition of rest, it may be inadequate during an effort: the physiological PR interval is shortened when heart rate increases, so a period of 300 ms may be acceptable in a state of rest, but it is much too long in a situation of an effort.

As illustrated in FIG. 2b, the device varies the limit delay MaxARhemo between a maximum value (designated MaxARhemo_max) applied when the heart rate $F_c$ is close to the base rate $F_{base}$, and a minimum value (designated MaxARhemo_min) when the heart rate $F_c$ is near the maximum heart rate $F_{max}$, preferably according to a linear function. In between each of these heart rates corresponds to an instantaneous value $F_c$ of the limit delay MaxARhemo beyond which the hemodynamic tolerance of the AVB1 is assessed.

FIG. 3 is a chart illustrating an implementation of the present invention within a device comprising an operating mode of the AAIsafeR type. This implementation is applicable mutatis mutandis to a device using an algorithm of adaptation of the hysteresis of the AVD.

The device operates in an AAI mode (block 10). The routine waits (block 12) for the completion of the ventricular cycle that is underway to analyze the state of conduction. The routine evaluates (block 14) if the criteria for suspected AVB1, AVB2 or AVB3 (or other criteria) are satisfied. These criteria are, for example:
 (a) first-degree AVB or AVB1 (conduction present but delayed): the number of atrial events followed by a ventricular detection occurs, for example, after a period of more than 350 ms (for a spontaneous atrial event) or 450 ms (for a stimulated atrial event) exceeding a given number, e.g., six consecutive cardiac cycles;
 (b) second-degree AVB or AVB2 (incomplete conduction, the gradual lengthening of the PR interval, or AR, such that a part of the P waves is no longer conducted): the number of atrial events not followed by a ventricular detection exceeds a certain number over the duration of a monitoring window extending over a predetermined number of atrial events: for example, when the device detects three non-consecutive blocked P waves among the twelve last cardiac cycles; and
 (c) complete AVB, third degree, or AVB3 (atrial waves, stimulated or spontaneous, totally blocked, that is to say, no longer followed by a ventricular depolarization): for example, succession of two atrial waves detected or stimulated, blocked or more than three seconds without any ventricular detection (situation of ventricular pause).

If any of these criteria (or other criterion) is verified, the algorithm switches the device into a DDD mode (block 16) in accordance with an AAIsafeR mode of operation.

However, if none of the detection criteria for AVB1, AVB2 and AVB3 is satisfied, the algorithm evaluates the length of the last N AR delays (block 18). According to a preferred embodiment, this assessment may correspond to the calculation of a mean value, in search of a maximum value within the N AR delays, or as in the present example, to the establishment of a criterion based on exceeding N consecutive AR delays of the instantaneous value of the threshold MaxARhemo, said MaxARhemo threshold being chosen so as to always be less than the threshold of a traditional AVB1 test (e.g., 350 or 450 ms).

If this criterion is satisfied, the patient is not experiencing AVB1 under the traditional criteria but is experiencing AVB1 against the test in accordance with the present invention. The algorithm then, according to the present invention, assesses the patient's tolerance to that AVB1 by triggering a monitoring of the hemodynamic tolerance (block 20, which will be discussed in detail with reference to FIG. 4). This occurs during the phase of monitoring of the hemodynamic tolerance that the algorithm forces the device to stay in an AAI mode, or otherwise imposes a switch to a DDD mode, depending on the result of the analysis of the hemodynamic tolerance.

If, however, the test evaluated in block 18 is not satisfied, the patient is not experiencing AVB1, thus no specific action is taken, and the algorithm returns to block 12 to analyze the next cardiac cycle.

FIG. 4 is a flowchart describing in detail how the follow-up of the hemodynamic tolerance is made corresponding to block 20 of FIG. 3 in a situation of AVB1 and in the presence of AR delays greater than the threshold value MaxARhemo.

First (block 22), the algorithm compares the current value of the index Indice_EA designated Indice_EA_encours, measured from the hemodynamic sensor, to the instantaneous reference value, Indice_EA_ref_encours. If the current index is greater than or equal to the reference value, the AVB1 is considered to be tolerated. There is no need to switch to a DDD mode and the algorithm returns (block 24) in block 12 of FIG. 3.

Otherwise, the algorithm switches to a DDD mode (block 26), with possible hysteresis to maintain a sufficient margin corresponding, for example, to the physiological variation in the signals.

In block 28, a counter is reset, which allows to maintain the DDD mode for a predetermined number of cycles. The counter is programmable to count, for example, 100 cardiac cycles.

In block 30, the algorithm waits until the next ventricular complex to update the data corresponding to the time spent in the DDD mode. In block 32, the counter is compared to the predefined value mentioned above (for example, 100 cardiac cycles). If this value is not reached, the device remains in the DDD mode, the counter is increased by one unit (block 34) and the algorithm returns to block 30.

Otherwise, the algorithm tests (block 36) whether the patient is in a phase of rest or exercise using the activity sensor of the device. If the patient is not at rest, then the device is held in the DDD mode until detection of a rest phase for the patient (back to block 30). Indeed, in patients with sinus dysfunction, the effort is one of the main factors triggering AVB1, so it is desirable to keep the DDD mode throughout an effort to optimize the tolerance during this phase.

Otherwise, when a rest condition is diagnosed at block 36, then the algorithm switches again the device in the AAI mode (block 38) and returns (block 40) in block 12 of FIG. 3 waiting for the next cycle.

FIG. 5 illustrates an exemplary flow chart for updating the reference values of the hemodynamic sensor. In one embodiment, this update is run in parallel to the procedures described above, and is executed when the device is in AAI mode, in the absence of detection of an AVB1. In another embodiment, the update procedure for the reference value is run independently by a separate algorithm, and the updated reference value is provided to the algorithm executing the procedures in FIGS. 3 and 4.

As explained above with reference to FIG. 2a, the reference index $EA_{ref}$ is adjustable between a minimum value Indice_EA_ref_repos and a maximum value Indice_EA_ref_exer. The current value Indice_EA_ref_encours varies between these two extremes. Initially, the algorithm waits until the end of the ventricular cycle underway to conduct the analysis (block 42). It then compares (block 44) the current AR delay to the current threshold MaxARhemo. If the AR delay exceeds the current threshold MaxARhemo, this means there is a situation of AVB1, and the reference data are not updated (as noted above, this update is made in the absence of detection of AVB1). The algorithm then returns to block 42 and waits for the next cycle.

In the absence of AVB1 when the AR delay does not exceed the current threshold MaxARhemo, the update procedure starts. First, the algorithm tests (block 46) if the patient is at rest or during exercise. If the patient is determined to be at rest, the algorithm includes in the overall calculation of Indice_EA_ref_repos the current value of Indice_EA_encours (block 48). This calculation can be, for example, a daily average, but the minimum or maximum value found at rest over a given period of time may be used for calculating and updating the value of Indice_EA_ref_repos. If the patient is active, the algorithm updates the value of Indice_EA_ref_exer.

To this purpose, a value maxEA is initialized with the current value of Indice_EA_encours (block 50). The algorithm is then put on hold until the next ventricular cycle (block 52) and compares again (block 54) the value of the delay AR to the current value of MaxARhemo, in the same manner as in block 44. If the delay AR exceeds MaxARhemo, this means that there is a situation of AVB1, and the update of the reference value is interrupted. Before completing the update, the algorithm compares Indice_EA_ref_exer to maxEA (block 56). If maxEA is greater than Indice_EA_ref_exer, the algorithm updates Indice_EA_ref_exer with this new value maxEA (block 58). Otherwise, the update is interrupted and the algorithm returns to block 42 waiting for the next cycle.

If, at block 54, the value of the delay AR is less than the current value of MaxARhemo, this means that there is no situation of AVB1, and the update procedure continues.

The algorithm checks if the patient is returned to rest (block 60). If this is the case, it terminates the update of the value of effort, and the reference values are updated in blocks 56 and 58 as described above under the condition of AVB1. In the opposite case (patient still in exercise), the algorithm compares (block 62) the value of Indice_EA_ref_encours to the value of maxEA. If maxEA is less than Indice_EA_ref_encours, the value of maxEA is updated with the new value Indice_EA_ref_encours (block 50), otherwise no update of maxEA is necessary and the algorithm waits (block 52) for the next cycle.

It is noted that the method described above provides for the reference index $EA_{ref}$ an average value at rest for the lower limit Indice_EA_ref_repos, and the maximum value at effort for the upper limit Indice_EA_ref_exer. Such a system would deviate over the iterations, so in order to avoid drifting of these values, the parameter maxEA is lowered by one increment at regular intervals (e.g. every 24 hours) to rebalance the system.

Implementation of the Invention in Case of a Permanent AVB1

The procedures that have just been described above in reference to FIGS. 3-5 are effective if the patient suffers from a paroxysmal AVB1, particularly in regard to learning of the reference values. In case of a permanent AVB1, however, it is impossible to update the index $EA_{ref}$.

It is therefore necessary to choose another reference index derived from the EA signal, such as a filling time. The reference index in this case is preferably a simple threshold value, which does not necessarily vary with heart rates F.

With reference to FIG. 6, in case of a permanent AVB1, the delays AR remain long while other conditions vary. For example, heart rate may increase resulting in a shortening of the RR interval ($RR_x < RR_y$). The parameter used to derive the EA signal is, for example, the delay AT separating the two endocardial acceleration peaks PEA1 and PEA2 of the EA signal during one cardiac cycle. These peaks are identified by temporal markers $T_{1EA}$ and $T_{2EA}$. The interval $\Delta T_x$ is compared to a reference threshold $\Delta T_{ref}$ and it is determined that AVB1 is tolerated if $\Delta T_x > \Delta T_{ref}$ and not tolerated otherwise. In the latter case, the algorithm switches the device to the DDD (or BiV) mode, as the situation of AVB1 requires the transition to this mode of stimulation. The rest of the operation, including the procedures to return to the AAI mode, may be identical as in the previous case discussed above.

In one embodiment, the time markers $T_{1EA}$ and $T_{2EA}$ are determined by implementing the technique described in European Application No. 09 209116.1 of 18 Feb. 2009 (US counterpart U.S. Pat. Pub. No. 2009/0209875), filed under priority of French application 08 00907 of 20 Feb. 2008, entitled "Device for the analysis of endocardial signal of acceleration", (ELA Medical, now Sorin CRM). This document describes how to determine the temporal position of various components associated with the heart sounds S1, S2, S3 or S4 of an EA signal of endocardial acceleration, including but not limited to, the components EA1 and EA2 or to the two "peaks" of endocardial acceleration PEA1 and PEA2. The interval ΔT is continuously calculated, either in absolute terms or by its variations relative to a cardiac mechanical component such as the filling time.

In FIG. 6, the patient is in a situation of AVB1, with a characteristic constant delay PR. However, as the heart rate progressively increases, the RR delay decreases ($RR_y<RR_x$), with decreasing hemodynamic delays ($\Delta T_y<\Delta T_x$). The threshold of tolerance $T_{ref}$ is chosen corresponding to the minimum filling time ensuring a satisfactory cardiac hemodynamic situation.

In FIG. 6, initially $\Delta T_x>\Delta T_{ref}$, which means that the AVB1 is tolerated, and the device remains in the AAI mode. However, later $\Delta T_y<\Delta T_{ref}$, which means that the filling time is insufficient. The AVB1 is thus not tolerated by the patient and the device operates a fall-back in the DDD (or BiV) mode (the subsequent return to the AAI mode using the same procedures as those described with respect to FIG. 4).

One skilled in the art will appreciate that the present invention can be practiced by embodiments other than those described herein, which are provided for purposes of illustration and not of limitation.

I claim:

1. An active implantable medical device for stimulation, resynchronization and/or defibrillation of a patient, comprising:
   means for detecting spontaneous atrial and ventricular events;
   means for delivering ventricular and atrial stimulation;
   means for detecting spontaneous ventricular depolarization after an atrial pacing;
   means for measuring an atrioventricular delay between the atrial pacing and the corresponding ventricular depolarization;
   means for operating the device in a dual chamber mode with ventricular sensing and ventricular pacing in the absence of spontaneous ventricular depolarization detected after an atrioventricular delay;
   means for mode switching, to control conditionally, according to a predetermined criteria, the switching of the device between a dual chamber mode and a pacing mode favoring a spontaneous atrioventricular conduction;
   a hemodynamic sensor having an output signal;
   means for deriving from the output signal a hemodynamic index representative of a patient's tolerance to the atrioventricular delay, wherein the means for deriving utilizes output data from the hemodynamic sensor associated with a single cardiac cycle to derive the hemodynamic index, wherein the means for deriving the hemodynamic index is configured to derive the hemodynamic index when the atrioventricular delay exceeds a threshold value; and
   means for inhibiting or forcing said conditional switching of the device to the dual chamber mode based on said hemodynamic index derived from the output data from the hemodynamic sensor associated with the single cardiac cycle.

2. The device of claim 1, wherein the pacing mode favoring the spontaneous atrioventricular conduction to the dual chamber mode comprises an AAI mode having a ventricular detection.

3. The device of claim 1, wherein the pacing mode favoring the spontaneous atrioventricular conduction to the dual chamber mode is one of a DDD mode and a biventricular mode having hysteresis of the atrioventricular delay.

4. The device of claim 1, further comprising means for diagnosing an occurrence of an atrioventricular block, wherein the means for inhibiting or forcing said conditional switching of the device to the dual chamber mode is selectively activated in the absence of atrioventricular block proved by the means for diagnosing.

5. The device of claim 1, further comprising:
   means for evaluating a current value of an interval between the atrial pacing and the consecutive spontaneous ventricular depolarization; and means for comparing said current value of the interval to the threshold value, wherein the means for inhibiting or forcing the conditional switching of the device to the dual chamber mode is selectively activated in response to the current value of the interval being greater than the threshold value.

6. The device of claim 5, wherein the threshold value comprises a variable threshold, depending on the heart rate of the patient, and the device further comprising means for dynamically reducing the value of the variable threshold when the current heart rate is increased.

7. The device of claim 1, further comprising means for detecting of a state of patient effort, wherein the means for inhibiting or forcing of the conditional switching of the device to the dual chamber mode further comprises means for forcing a switch to the dual chamber mode, and inhibiting a return back to the pacing mode favoring the spontaneous atrioventricular conduction until the device detects a state of patient effort.

8. The device of claim 1, wherein the means for inhibiting or forcing the conditional switching of the device to the dual chamber mode further comprises means for comparing the current value of the hemodynamic index to a reference hemodynamic index, wherein the means for forcing switches the device to the dual chamber mode when the current value of the hemodynamic index is less than the reference hemodynamic index.

9. The device of claim 8, wherein the value of the reference hemodynamic index is a variable value depending on the heart rate of the patient, and the device further comprises means for dynamically increasing the value of the reference hemodynamic index when the current heart rate is increased.

10. The device of claim 9, wherein the value of the reference hemodynamic index is a variable value between a minimum limit and a maximum limit, and the device further comprises means for dynamically updating said minimum and maximum limits.

11. The device of claim 8, further comprising:
    means for determining an occurrence of a permanent atrioventricular block, and
    means for forcing the reference hemodynamic index to a value independent of the heart rate in the presence of a determined permanent atrioventricular block.

12. The device of claim 1, wherein the hemodynamic sensor further comprises a sensor selected from among the group consisting of an endocardial acceleration sensor, an epicardial acceleration sensor, a myocardium wall motion sensor, an intracardiac pressure sensor, an intracardiac bioimpedance sensor, an optical sensor measuring oxygen saturation, and a sensor for measuring a change in volume by ultrasounds.

13. The device of claim 12, wherein the hemodynamic sensor is a hemodynamic endocardial acceleration sensor, delivering the output signal representative of the movements produced by the cyclical contractions of the myocardium.

14. The device of claim 13, further comprising:
means for recognizing and isolating in the output signal a component corresponding to a peak endocardial acceleration associated with a ventricular contraction, and means for deriving said hemodynamic index from said component.

15. The device of claim 13, further comprising:
means for recognizing and isolating in the output signal delivered by the hemodynamic sensor at least two components corresponding to two respective peaks of endocardial acceleration associated with the ventricular contraction, and
means for deriving said hemodynamic index from a time interval separating the at least two components.

16. The device of claim 1, wherein said dual chamber mode comprises a DDD mode.

17. The device of claim 1, wherein said dual chamber mode comprises a biventricular mode.

18. The device of claim 1, wherein:
said hemodynamic sensor comprises a hemodynamic endocardial acceleration sensor;
said output signal is representative of movements produced by cyclical contractions of a myocardium;
said means for deriving from the output signal a hemodynamic index is configured to derive said hemodynamic index from a component in the output signal corresponding to a peak endocardial acceleration associated with a ventricular contraction; and
said means for inhibiting or forcing said conditional switching of the device to the dual chamber mode is configured to determine whether to place the device in the dual chamber mode based on the hemodynamic index derived from the component in the output signal corresponding to the peak endocardial acceleration associated with the ventricular contraction.

19. An implantable medical device comprising:
a hemodynamic sensor configured to generate an output signal, wherein the hemodynamic sensor comprises an electronic sensor configured to measure a value representative of a property of at least one of heart tissue and blood flowing through a heart or blood vessels proximate to the heart; and
one or more circuits configured to:
switch the implantable medical device between a single chamber mode and a dual chamber mode, wherein, in the single chamber mode, the one or more circuits are configured to stimulate the atrium and prompt spontaneous atrioventricular conduction, and wherein, in the dual chamber mode, the one or more circuits are configured to stimulate the ventricle in the absence of spontaneous ventricular depolarization detected after an atrioventricular delay,
measure the atrioventricular delay between an atrial pacing event and a spontaneous ventricular depolarization after the atrial pacing event,
determine whether the atrioventricular delay exceeds a threshold atrioventricular delay,
in response to the atrioventricular delay exceeding the threshold atrioventricular delay:
derive from the output signal of the hemodynamic sensor a hemodynamic index representative of a patient's tolerance to the atrioventricular delay that exceeds the threshold atrioventricular delay, and
determine whether to activate or deactivate the dual chamber mode based on the hemodynamic index.

20. The device of claim 19, wherein the single chamber mode comprises an AAI mode having a ventricular detection.

21. The device of claim 19, wherein the hemodynamic sensor is configured to measure one or more of an endocardial acceleration value, an epicardial acceleration value, a myocardium wall motion value, an intracardiac pressure value, an intracardiac bioimpedance value, an oxygen saturation value, or a volume change value.

22. An implantable medical device comprising:
a hemodynamic sensor configured to generate an output signal; and
one or more circuits configured to:
switch the implantable medical device between a single chamber mode and a dual chamber mode, wherein, in the single chamber mode, the one or more circuits are configured to stimulate the atrium and prompt spontaneous atrioventricular conduction, and wherein, in the dual chamber mode, the one or more circuits are configured to stimulate the ventricle in the absence of spontaneous ventricular depolarization detected after an atrioventricular delay,
determine, over a plurality of atrial events, whether an amount of atrial events that are not followed by a detected ventricular event exceeds a threshold,
in response to the number of atrial events that are not followed by a detected ventricular event exceeding the threshold, activate the dual chamber mode,
in response to the number of atrial events that are not followed by a detected ventricular event not exceeding the threshold, determine whether to activate or deactivate the dual chamber mode using the hemodynamic sensor by:
deriving from the output signal of the hemodynamic sensor a hemodynamic index representative of a patient's tolerance to the atrioventricular delay when the atrioventricular delay exceeds a threshold value, and
determining whether to activate or deactivate the dual chamber mode based on the hemodynamic index.

* * * * *